(12) United States Patent
Evans

(10) Patent No.: US 6,971,257 B1
(45) Date of Patent: Dec. 6, 2005

(54) MACHINE FOR TESTING WEAR, WEAR-PREVENTATIVE AND FRICTION PROPERTIES OF LUBRICANTS AND OTHER MATERIALS

(76) Inventor: Paul R. Evans, 5S342 Scott Rd., Big Rock, IL (US) 60511

(*) Notice: Subject to any disclaimer, the term of this patent is extended or adjusted under 35 U.S.C. 154(b) by 0 days.

(21) Appl. No.: 11/023,206

(22) Filed: Dec. 27, 2004

Related U.S. Application Data

(62) Division of application No. 10/010,428, filed on Nov. 30, 2001, now Pat. No. 6,840,082.

(51) Int. Cl.[7] .............................................. G01N 3/56
(52) U.S. Cl. ......................................................... 73/7
(58) Field of Search ............................... 73/7–10, 818, 73/825

(56) References Cited

U.S. PATENT DOCUMENTS

| | | | |
|---|---|---|---|
| 2,019,948 A * | 11/1935 | Boerlage | 73/10 |
| 2,370,606 A | 2/1945 | Morgan et al. | |
| 2,539,578 A | 1/1951 | Headley | |
| 3,045,471 A | 7/1962 | Chapman et al. | |
| 3,302,447 A | 2/1967 | Mertwoy et al. | |
| 3,324,708 A | 6/1967 | Staph et al. | |
| 3,380,288 A | 4/1968 | Bradley | |
| 3,939,690 A | 2/1976 | Kuss et al. | |
| 4,133,200 A | 1/1979 | Cray | |
| 4,228,674 A * | 10/1980 | Mertwoy | 73/10 |
| 4,700,610 A | 10/1987 | Bauer et al. | |
| 4,958,511 A * | 9/1990 | Marcus | 73/7 |
| 4,966,030 A * | 10/1990 | Kobayashi et al. | 73/7 |
| 5,072,611 A | 12/1991 | Budd et al. | |
| 6,412,330 B1 * | 7/2002 | Dicello et al. | 73/7 |

OTHER PUBLICATIONS

Falex, "Four-Ball Wear Test Machine" (Falex Four-Ball Wear Machine ASTM D2266, D4172, and D5183).
Falex, "Four-Ball Extreme Pressure Test Machine" (Falex Four-Ball Extreme Pressure Test Machine ASTM D2596, D2783).
Falex Corp "Falex Multi-Specimen Test Machine", 3 pages, Oct. 31, 1995.
ASTM D 2266-91, 3 pages.
ASTM D 2596-93, 5 pages.
ASTM D 2783-88 (Reapproved 1998), 8 pages.
ASTM D 4172-88, 4 pages.

* cited by examiner

*Primary Examiner*—Robert Raevis
(74) *Attorney, Agent, or Firm*—Keith Frantz

(57) ABSTRACT

A machine adapted for testing wear, wear-preventative and friction characteristics between a rotating specimen axially loaded against one or more non-rotated test specimens includes a load mechanism in the form of a low-friction, pneumatic diaphragm actuator, a load sensor in the load path to provide visual confirmation and feedback for automated load control, a linear motion sensor aligned with the load path for detection of specimen wear during the test, and a torque sensor for detection of the friction generated between the test specimens.

13 Claims, 7 Drawing Sheets

MACHINE FOR TESTING WEAR, WEAR-PREVENTATIVE AND FRICTION PROPERTIES OF LUBRICANTS AND OTHER MATERIALS

CROSS-REFERENCES TO RELATED APPLICATIONS

This application is a divisional of and claims the filing date benefit of U.S. patent application Ser. No. 10/010,428, filed Nov. 30, 2001. now U.S. Pat. No. 6,840,082.

INCORPORATION-BY-REFERENCE OF MATERIAL SUBMITTED ON A COMPACT DISC

Not Applicable.

STATEMENT REGARDING FEDERALLY SPONSORED RESEARCH OR DEVELOPMENT

Not Applicable.

BACKGROUND OF THE INVENTION

1. Field of Invention

The present invention relates generally to machines adapted to test the wear, wear-preventative and friction properties of oils, grease, dry-film lubricants and other lubricants, and both lubricated and non-lubricated materials.

More particularly, the invention relates to machines of a type adapted to test such properties between a rotating test specimen loaded against one or more non-rotated, generally stationary test specimens in a direction along the axis of rotation of the rotating specimen.

2. Background Art

A common conventional test machine of the subject type typically used for testing the wear preventative characteristics of lubricants is known as a four-ball test machine. In particular, four-ball test machines are generally used to conduct two basic types of testing: a wear test, and extreme pressure tests.

During a typical wear test in a four-ball test machine, one ball is rotated against three non-rotated, generally stationary balls under predetermined time and load conditions. The balls are coated with or immersed in a test lubricant during the test, and the wear patterns on the balls are analyzed after the test to determine the wear-preventive characteristics of the lubricant.

Standardized test methods of this general type are explained more fully in ASTM D 2266, Standard Test Method for Wear Preventive Characteristics of Lubricating Grease (Four-Ball Method); and ASTM D4172, Standard Test Method for Wear Preventive Characteristics of Lubricating Fluids (Four-Ball Method).

Common extreme pressure tests, conducted under relatively high loads, include: a weld-point test to determine at what test load the balls seize-up or weld together with the lubricant being tested, and a load-wear index test to determine an index of the ability of the lubricant to prevent wear at an applied load.

Standardized test methods for tests of this general type are explained more fully in ASTM 2596, Standard Test Method for Measurement of Extreme-Pressure Properties of Lubricating Grease; and 2783, Standard Test Method of Extreme-Pressure Properties of Lubricating Fluids (Four-Ball Method).

A conventional four-ball test machine includes a ball chuck to hold the ball to be rotated, and a ball pot in which the three stationary balls are held and which is sized to immerse the test balls when testing a liquid lubricant. The stationary balls are held centered about the axis of rotation of the ball chuck, and the rotated ball is loaded against the three stationary balls with a test force or load acting along the axis.

In a lever-loaded machine, the test load is applied to the balls with the use of weight at one end portion of a lever-arm. The lever arm is fulcrumed in the machine such that the other end engages a linear acting rod or pin which in turn axially loads the balls through a thrust bearing and thrust plate.

In setting up for a test, the operator manually positions a weight to act over a lever-arm length to obtain the desired load condition on the balls. The test load is adjusted by adjusting the weight and its position along the length of the lever, and is determined by the weight and a standard lever formula associating the ratio of the distances from the fulcrum to the weight and to the load rod.

There are several disadvantages and drawbacks associated with the use of conventional, lever-loaded wear test machines. In particular, it is well known that the test results obtained with a conventional lever-loaded four-ball test machine are not accurately repeatable. This is particularly true as between different test setups. See e.g., discussion of repeatability of test results in ASTM D 2266.

The inability to accurately reproduce test results with conventional four-ball test machines is due to several factors, including:

(i) Non-Reproducibility of Test Load Conditions—An operator is often unable to accurately reproduce load conditions between different test setups, whether on different machines or the same machine because, among other things, of possible load error and positioning error in manually selecting and positioning the load on the arm, and because the machines do not provide confirmation of the load condition established by the operator prior to conducting a test.

(ii) ASTM accepted accuracy for an applied load is only approximately +0.5% (e.g., +0.2 kg at 40 kg load).

(iii) Operator Dependency—Test results are also dependent upon the operator conducting the test. See e.g., ASTM D 2266, paragraphs 11.2.1 and 11.2.2 in which anticipated differences between test results are shown to be higher with different operators than with the same operator, using the same test setup.

(iv) Friction Induced Error—The rod that transfers the load from the lever to the test balls is subject to a stick-slip friction condition, resulting from side-loading of the rod against its guide bore and other components such as contacting the ends of the rod. In addition to other effects, and as discussed further below, this friction makes it difficult to obtain the same test load from one test setup to another, and maintain a constant load during the test as the specimen wears. As a result, the stick-slip friction problem lowers the sensitivity, accuracy and repeatability of the test machine.

Linear wear between the test specimens during a test is another indicator of the characteristics of the lubricant under test. However, the measurement of linear wear with conventional lever-loaded wear test machines is not accurately repeatable between tests.

Measurement of linear wear in a conventional test machine is accomplished indirectly with an LVDT that extends parallel to but is offset from the axis of the applied load. The LVDT is connected between a stationary frame member of the machine, and the outer end of a small lever that engages the ball pot assembly at the other end for linear movement therewith, and that extends radially outwardly therefrom to the LVDT.

However, variable and unpredictable vibration occurring during a test, and amplification of the vibration along the length of the small lever arm, introduces errors into the setup, which results in LVDT sensing and indication of linear wear that is not the true wear between the test specimens. Thus, use of such arrangements does not provide linear wear data with a high degree or accuracy, but only provides a relatively rough indication of linear wear during a test.

In addition, the load range of a conventional lever-loaded four-ball wear test machines is limited, being typically rated for a maximum test load of approximately 60 kg. This load range is insufficient to weld most materials, and thus, the conventional four-ball test machines are not capable of conducting the extreme pressure test that are also indicative of lubrication and wear characteristics. Therefore, if both conventional wear tests and extreme pressure tests are to be conducted, a second test machine capable of conducting the extreme pressure tests is required.

The friction induced test deficiencies are due, in part, to relatively small clearances in the lever-loaded wear test machine. In particular, the clearance between the load pin and the bore in which it is guided is relatively small. As a result of this small clearance, any side-loading on the pin results in friction between the pin and the bore. Side-loading also results in friction between the ends of the pin and its supporting components, including a thrust disk that transmits the load on through to the balls at one end of the lever.

In practice, the side-loaded pin exhibits a condition that is commonly known as a "stick-slip" condition. This condition occurs with a relatively high static friction coefficient as compared with the dynamic friction coefficient. As a consequence, the static friction must be overcome before the pin will begin to move. In other words, as a result of the stick-slip friction condition, a relatively high change of force must occur before the rod can move to maintain a constant load condition as the specimen wears. This is a condition that can cause problems both before and during a test.

Before the test, as the load is adjusted prior to a test, the full change in load may not reach the test balls if it is insufficient to overcome the static friction; and even when sufficient to overcome the static friction, a portion of the load change may be lost as reacted against by the static friction. In other words, loading of the lever with the weights exhibits a hysteresis band between the change in load from the lever and the load carried through to the balls. Consequently, it can be difficult to obtain the same test load from one test setup to another, even if the same weight is placed in precisely the same position on the lever.

And the balls wear during a test. This wear causes two direct consequences: (i) the load mechanism must move to maintain a constant load on the balls, and (ii) the surface of the balls becomes rough. In order to maintain a constant load on the test balls, the pin must move toward the balls. However, the stick-slip condition can prevent the pin from moving smoothly during a test to maintain a constant load.

The balls do not wear evenly during a test. This uneven wear can result in further side-loading of the pin against the guide bore. This side-loading is unpredictable and can change throughout the test, resulting in a changing test load during the test and further unrepeatability of test results.

This stick-slip condition reduces the sensitivity of the machine to changes in load, and thus reduces the ability to accurately control the load both before and during the test. Thus, it is apparent that conventional lever-loaded four-ball wear test machines are incapable of providing accurately repeatable test data, but rather provide only a relative indication of such data within relatively wide limits.

In addition to the conventional wear and extreme pressure tests, accurate real-time data as to linear wear of the test balls would be instructive as to and assist in determining additional parameters of the wear, wear-preventative and friction characteristics of the lubricant or material under test. However, conventional four-ball test machines are incapable of providing such data.

An alternate four-ball test machine uses a pneumatically actuated piston that is slidably located in a guide bore to load the test balls. In an effort to keep the friction low, this pneumatic operator does not use a piston seal, but instead relies on a relatively snug fit between the piston and the bore. However, this type of load mechanism is also subject to stick-slip friction as the piston attempts to slide during a test, resulting from side loading against the bore as the balls wear. In addition, the load range of this alternate test machine is typically limited to approximately 180 kg, and is thus inadequate to conduct the extreme pressure tests. This machine is also incapable of providing direct wear data with a high degree of accuracy during a test.

Extreme Pressure (EP) four-ball test machines are typically rated for maximum load conditions of approximately 1000 kg and are used to conduct the extreme pressure tests.

The construction of an EP lever-loaded four-ball test machine is similar to the conventional lever-loaded four-ball test machines, except that the lever and associated actuating and loading components in the load path are constructed for the higher loads. However, conventional lever-loaded EP test machines also present several disadvantages and drawbacks. Although capable of conducting the weld-point test, it can be an extremely inefficient, time consuming and costly test as conducted on an EP machine.

The procedure for conducting a weld-point test on an EP machine involves first establishing a predetermined load, and running the balls under that load against the rotating ball for a predetermined time such as ten seconds.

If the test balls did not seize-up during the ten second run, the machine is turned off, new balls and test lubricant are put into the test machine, an increased load is established by adjusting the weight and/or the location of the weight along the lever arm, and the test is run for another ten seconds.

This procedure is repeated, with incrementally increasing loads, until the test balls seize during the ten second run; the load at which the balls seize being deemed the weld-point threshold of the lubricant under test. Without repeating the testing by reducing the load conditions in smaller increments, the test provides only a minimum threshold that the lubricant passed; it does not establish the actual load at which the balls would seize together. And determining the load-wear index is based on several applied loads immediately preceding the weld point. (See e.g., ASTM D 2596, Sect. 10.2 Load-Wear Index). Thus, determining the weld-point on an EP machine is a slow, repetitive, and expensive process that typically only establishes a minimum weld-point threshold, and conducting the load wear index test is based on the repetitive nature of the weld-point test.

The load accuracy and sensitivity of EP machines are even worse that the accuracy and sensitivity of the conventional wear test machines. The load accuracy of an EP machine is typically approximately +1 kg or greater. Therefore, EP machines are not suitable for accurately conducting the conventional wear testing under the lighter load conditions of conventional four-ball wear test machines. Thus, to conduct both low load wear testing and high load extreme pressure testing requires the use of two different machines, and the associated cost for purchasing both machines.

The accuracy and sensitivity of EP machines, and the repeatability of test results, are further reduced due to friction inherent in the design of the machine. As with the conventional four-ball wear test machines, the load pin experiences a stick-slip condition from side thrust imparted by the lever onto the pin against the side of the bore, and from uneven wear of the balls.

However, the higher load and wear conditions in an EP test machine enhance the effect of friction (i.e., the side-loading and resulting friction between the rod and the bore is enhanced), and thus the stick-slip condition is enhanced on EP machines.

As with the conventional wear test machines, EP test machines do not include provision for detecting with a high degree of accuracy the linear wear of the balls or torque during the test. However, of further concern in an EP machine, the lack of wear detection can result in damage to the machine. When the balls experience excessive wear, the skirt of the rotating chuck can contact the stationary balls. This results in damage to the chuck which must then be replaced, as well as loss of associated part and labor cost and downtime of the machine.

Damage to the chuck also presents the possibility of substantial damage to the machine when the chuck loses the ability to firmly hold the rotated ball. In which case, additional parts must be replaced, resulting in greater expenses and losses associated therewith.

EP machines are also subject to severe vibration problems, further reducing the accuracy and repeatability of the test results. As previously mentioned, the balls wear unevenly, and the surface finish of the balls becomes rough during a test. The rotation of balls having a rough surface finish against each other causes the machine components in the load path to vibrate. With the relatively high loads, this vibration level can become substantial during testing on an EP machine.

This high vibration is variable and unpredictable, and in many instances, is further amplified as the frequency of vibration approaches the natural frequency of the lever and load path components, and/or from the stick-slip friction phenomenon which can contribute to a dynamically unstable condition.

As a result, often times during EP machine extreme pressure testing, the load-path components bounce back and forth with relatively high amplitude. This high amplitude vibration, including bouncing of the weighted lever results in impact loading between the balls during the test, and further contaminates the test, complicates analysis of the test results, and reduces the repeatability of such results.

Yet another type of four-ball test machine, is a multi-specimen machine that uses either two or four pneumatic diaphragm operators to load the test balls. The pneumatic operators are located radially outwardly of the rotational axis of the rotated ball at an equal distance, are equally spaced from one another.

Although this type of machine offers certain potential improvements as compared with conventional lever-loaded wear and extreme pressure test machines, it also suffers from certain drawbacks and disadvantages that prevent it from fully implementing or realizing those potential improvements.

The multi-specimen test machine does not provide for direct measurement of the load or wear during a test. This machine senses the pressure in the pneumatic operators to determine the load on the balls. Therefore, control of the test load is subject to response errors, and the load information that is available is not accurate on a real-time dynamic basis, as it is subject to a lag, both resulting from the compressibility of the air in the pneumatic actuators.

In addition, the multi-specimen has a relatively high number of friction points, including two friction points on the load rod, and point of friction for each of the load cylinders. Thus results in a test machine with a relatively high hysteresis characteristic in the load system of the machine.

This multi-specimen test machine is typically rated for test load range of approximately 2,000 lb. Therefore, the load operators of the machine are capable of providing sufficient load to conduct the extreme pressure tests. However, as constructed, the load path components of the multi-specimen test machines preclude safely conducting the extreme pressure tests.

In particular, the structural characteristics of the spindle assembly of the multi-specimen machine are incapable of safely supporting the rotating ball against the high loads of the extreme pressure tests, because of the spindle design. The spindle has a long, relatively narrow portion between support bearings associated with the housing and the mounting end for the upper test specimen. As a result, the mounting end flexes and does not allow for table positioning of the upper test specimen, particularly under extreme-pressure load conditions.

From the foregoing discussion, it is clear that there is a need for a new and improved four-ball test machine that addresses the above-identified disadvantages and undesirable characteristics of conventional prior four-ball test machines.

In particular, there is a need for a machine that eliminates the stick-slip condition of prior test machines, and the friction induced problems associated therewith; eliminates or reduces the vibration induced problems associated with prior machines; provides for application of an accurate and repeatable test load condition, and for direct measurement of the test load condition in real-time for visual or other confirmation or control thereof; eliminates operator dependency in the application of the test load, and in the test results with visual feedback of actual load conditions to the operator, and/or with automatic control of the test load; provides improved load range capability to enable conducting both wear and extreme pressure tests on the same machine resulting in substantial cost savings over having to purchase and maintain two different machines; provides improved efficiency in conducting the extreme pressure tests, including accurately determining the actual weld-point threshold and improving accuracy of the load-wear index data; and provides direct measurement of wear and torque generated during a test, to preclude the possibility of damage to the machine due to excessive specimen wear, and to permit determination of additional test-result parameters and characteristics.

SUMMARY OF THE INVENTION

The general objective of the present invention is to provide a new and improved four-ball test machine adapted to provided enhanced load control accuracy and repeatability of test results as compared with prior four-ball test machines.

A detailed objective is to achieve the foregoing by providing for controlled loading conditions with the use of a low friction, low hysteresis, variable, pneumatically damped, load mechanism, and for a low friction, linearly guided load pin.

Another objective of the invention is to provide a four-ball test machine that is adapted for increased load range capability, thus eliminating the need to use two different machines to conduct tests over a wide range of test conditions.

Yet another objective of the invention is to provide a four-ball test machine that is capable of maintaining the test load and other test input parameters constant, or alternately automatically increasing and decreasing test parameter characteristics such as load conditions, fluid temperature and velocity, in a controlled, accurate, and consistent manner during a test.

Still another objective of the invention is to provide a four-ball test machine adapted for directly measuring the load condition during a test, to provide visual or printed confirmation of the load condition and/or for use in a feedback control system.

An additional objective of the invention is to provide a four-ball test machine that is capable of directly measuring both the linear wear and the torque generated during a test.

These and other objectives and advantages of the invention will become more apparent from the following detailed description when taken in conjunction with the accompanying drawings.

Briefly, a four-ball test machine in accordance with the invention includes a ball chuck to hold the ball to be rotated, and a ball pot assembly that includes a ball pot in which the three non-rotated, generally stationary balls are held and which is capable of holding sufficient lubrication to immerse the test balls during a test.

An electric motor is connected to a drive shaft to rotate the ball chuck and test ball therein, and a pneumatic diaphragm loading mechanism is connected to establish the compressive test load between the rotating ball and the stationary balls.

The pneumatic diaphragm load mechanism is a low-friction, linear-acting actuator such that testing is conducted under controlled, predictable, repeatable load conditions by controlling the pressure in the actuator.

The load pin coupled between the pneumatic actuator and the test balls is linearly guided in a low friction linear rolling element bearing. This, combined with the low-friction, pneumatic actuator, eliminates the stick-slip and other friction related conditions that adversely affect sensitivity and repeatability of prior four-ball testing machines. As a result, the test machine in accordance with the invention results in improved accuracy, sensitivity and repeatability of test conditions.

The diaphragm is a "damped" load operator as compared to the prior lever-loaded machines. This damping raises the natural frequencies of the load-path components, and therefore stabilizes the mechanism at higher frequencies. This damping also de-amplifies the vibration that results as the surface finish of the balls deteriorates.

The test load is established by the pressure in the pneumatic operator, the pressure is established by a pressure regulating control valve, and in certain preferred embodiments, an electronic controller is preferably coupled to the pressure control valve for automated control of the test load conditions.

The pneumatic actuator is sized for providing a wide range of load conditions such that the machine is capable of conducting both conventional wear testing and weld-point testing. This eliminates the prior need to purchase and use two different machines for the two different types of tests.

The pressure control valve is manually and/or automatically controllable. The manual control is established with either a valve that is manually operable, or a valve controlled by an electronic controller that is manually set to a desired setpoint.

The manual controllability permits conducting conventional wear testing under various load conditions as desired. And in combination with the visual indication or controlled feedback of the actual test load conditions discussed further below, the manually set load conditions can be accurately repeated between different test setups.

The controller is also programmable for various automated, completely controlled test conditions, and for conducting such testing with appropriate safety features. This permits conducting a test under both constant and variable controlled load conditions, For example, this enables conducting a test under both controlled increasing and decreasing test load conditions, and controlled oscillating, as well as constant load conditions. This also enables conducting a weld-point test with one test setup by increasing the test load continuously and/or at a controlled rate during the test until the balls seize.

As a result, determination of the weld-point of the lubricant under test is more accurately and easily determined, and requires only one test run. The speed and efficiency of conducting the weld-point test is substantially enhanced as compared with conducting the test on prior EP machines, and the cost of conducting the test is substantially reduced.

This also enables conducting the weld-point test under additional test conditions previously unavailable, such as determination of the weld-point based on the dynamic rate of increase of the test load. Also enables conducting wear testing under variable, as well as constant load conditions, being able to control both the load as well as the rate of change of the load.

The controller also permits conducting additional tests that can not be conducted on prior four-ball test machines. For example, the controller makes possible a "wear-point" test that is conducted by increasing the load at a constant rate (i.e., providing a ramp-load) until wear initiates.

A load sensor is connected in-line in the load path of the machine (i.e., in-line with the applied test load), preferably between the actuator and the ball pot assembly to provide direct indication of the actual test load prior to and during a test. This enables providing accurate, real-time visual and/or printed confirmation of the test load prior to conducting the test, and enables automatic control of the test load with a feedback control system.

A torque-sensor is also connected to the ball pot assembly to detect the torque generated between the stationary and rotating balls during the test. This enables, for example, the ability to provide friction force indication and coefficient of friction indication dynamically during a test.

A linear motion sensor is mounted, preferably aligned with the applied test load, to directly detect the axial motion of the load pin. This enables direct, reliable, real-time detection and determination of the axial wear between the balls during the test.

Detection of linear wear allows a test to be stopped before the rotating chuck contacts the stationary balls. In this instance, as dimensional cut-off point is established and programmed into the load controller. This precludes the potential for damage to the machine as is present in conventional EP test machines, and saves the cost associated with replacement of damaged chucks and other damaged machine parts.

Detection of linear wear on a real-time basis also permits analysis and determination of a wide variety of additional characteristics of wear, wear-preventative and friction characteristics, including: wear of test balls vs. time, wear of test balls vs. speed of rotation, wear of test balls vs. temperature of lubricant, wear of test balls vs. load characteristics for static load changes, wear of test balls vs. load characteristics for dynamic load changes, the above-mentioned test parameters and characteristics vs. friction forces and coefficient of friction, the above-mentioned test parameters and characteristics vs. torque generated during a test, and additional test parameters and indicators of lubrication properties.

In combination with numeric manipulation in a data analysis unit, detection of linear wear on a real-time basis also permits the biasing out of factors such as expansion due to temperature changes, as controlled by a heater assembly, in the test balls, and linear compression of the test balls to arrive at actual linear wear data with a high degree of accuracy. And when combined with other appropriate hardware, can provide graphical and printed data.

Thus, the test machine in accordance with the invention provides enhanced repeatability of test load conditions and thus test results, over a wider range or test loads, and provides for the collection and determination of substantially more test data that is simply not available from prior test machines because of their friction and vibration problems.

Figure 1:
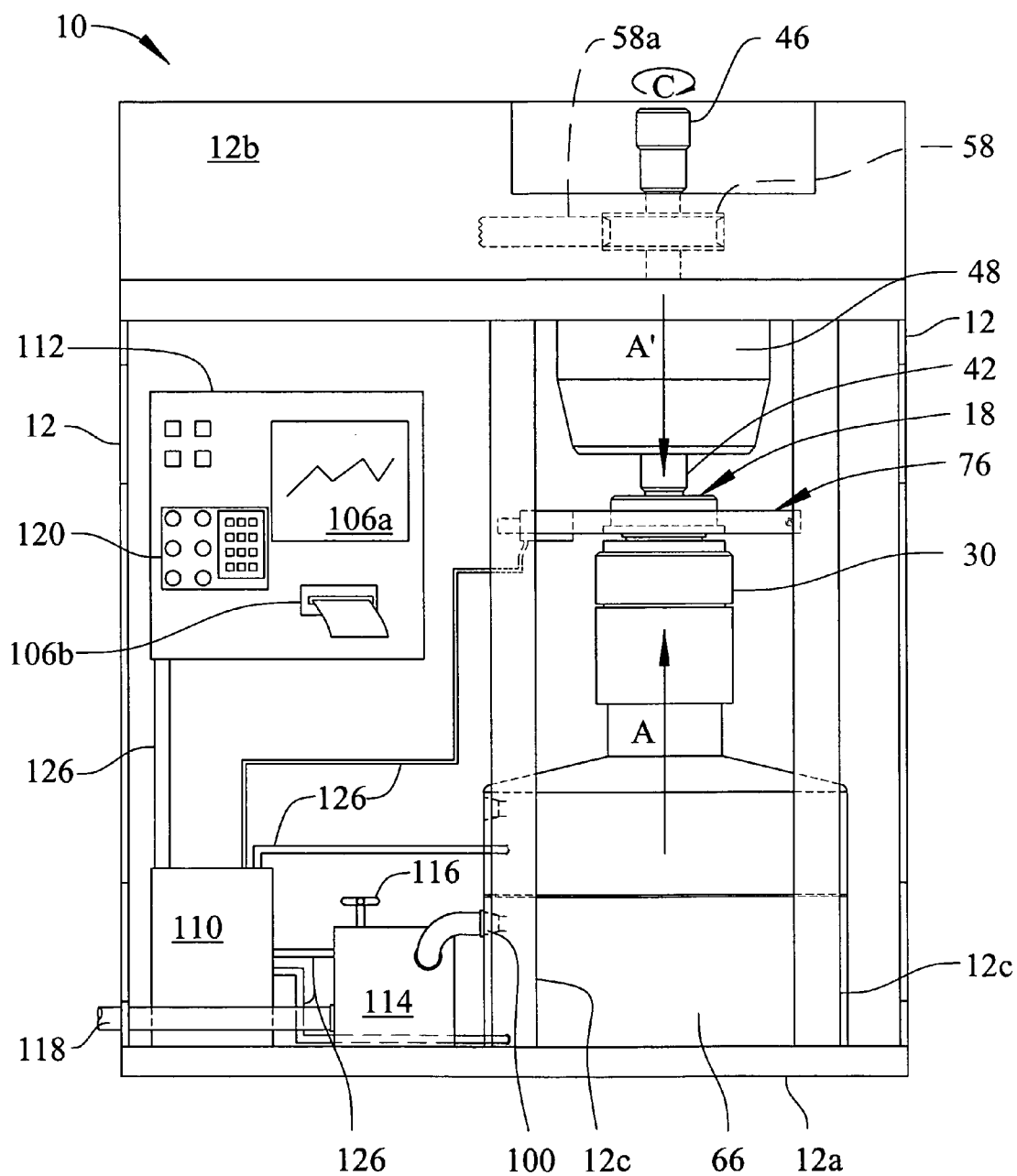
FIG. 1 is a front view of a four-ball test machine incorporating the unique aspects of the present invention
Figure 2:
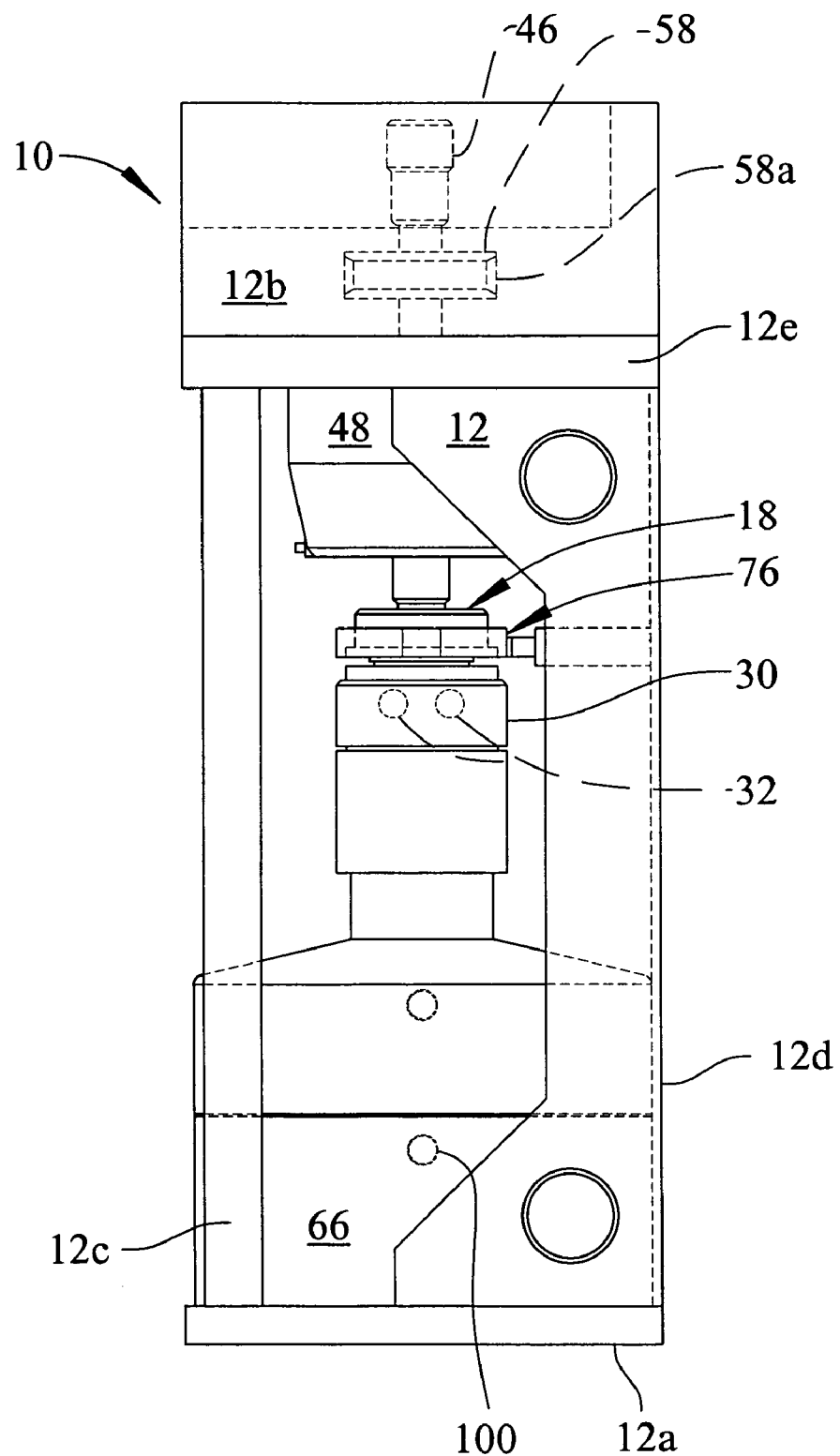
FIG. 2 is side view of the test machine of FIG. 1.

Reference numerals shown in the drawings correspond to the following items discussed in detail below:
10 four-ball test machine
12 frame
12a base plate
12b sheet metal guard for drive belt
12c tension posts
12d back plate
12e upper plate
14 rotated test ball
16 stationary test balls
18 ball pot assembly
20 ball pot
22 lock nut
24 tapered ring
26 thrust plate
30 ball pot mounting disc/aluminum block of heater
32 cartridge heater
34 thrust bearing
36 inverted upper race of thrust bearing
38 collet (ball chuck)
40 collet seat
42 rotary drive shaft
44 draw bar
46 threaded cap/knurled nut
48 spindle housing
50 radial bearings
52 thrust bearings
054 torque lever arm
56 force transducer
58 pulley
58a drive belt
60 connecting member
62 rolling member (e.g., wheel, ball bearing)
62a outer radius profile of rolling member 62
64 calibrating arm
66 actuator
68 actuator load-rod
70 actuator housing
72 actuator base
74 threaded fasteners
76 torque sensing assembly
78 piston
80 guide tube
82 load sensor
84 diaphragm
84a outer rolling portion of diaphragm 84
84b inner rolling portion of diaphragm 84
86a outer diaphragm retaining ring
86b inner diaphragm retaining ring
88a linear bearing
88b linear bearing
90 annular pressure chamber
92 vented chamber
94 vented chamber
96 vent to atmosphere
98 vent to atmosphere
100 air inlet port
102 LVDT (linear position sensor)
104 plunger
106a visual/graphic read-out device
106b recording/print-out device
108 control module
110 control unit
112 electronic data analysis unit
114 pressure regulating valve
116 valve handle for manual pressure control
118 air pressure supply connection
120 input reference signal module
122 safety-watch module
124 LVDT safety reference signal
126 electrical wiring
128 speed sensor
130 temperature sensor
A direction of load applied by actuator
A' direction of reaction of test load by drive shaft
A—A' axis of applied test load
B lever-length of torque sensor 76
B' lever-length of calibrating arm 64

C rotation of drive shaft and test ball 14

D—D axis of wheel 62 in torque sensor

While the invention is susceptible of various modifications and alternative constructions, a certain illustrated embodiment has been shown in the drawings and will be described below in detail. It should be understood, however, that there is no intention to limit the invention to the specific form disclosed, but on the contrary, the intention is to cover all modifications, alternative constructions, and equivalents falling within the spirit and scope of the invention.

DETAILED DESCRIPTION OF THE INVENTION

Figure 3:
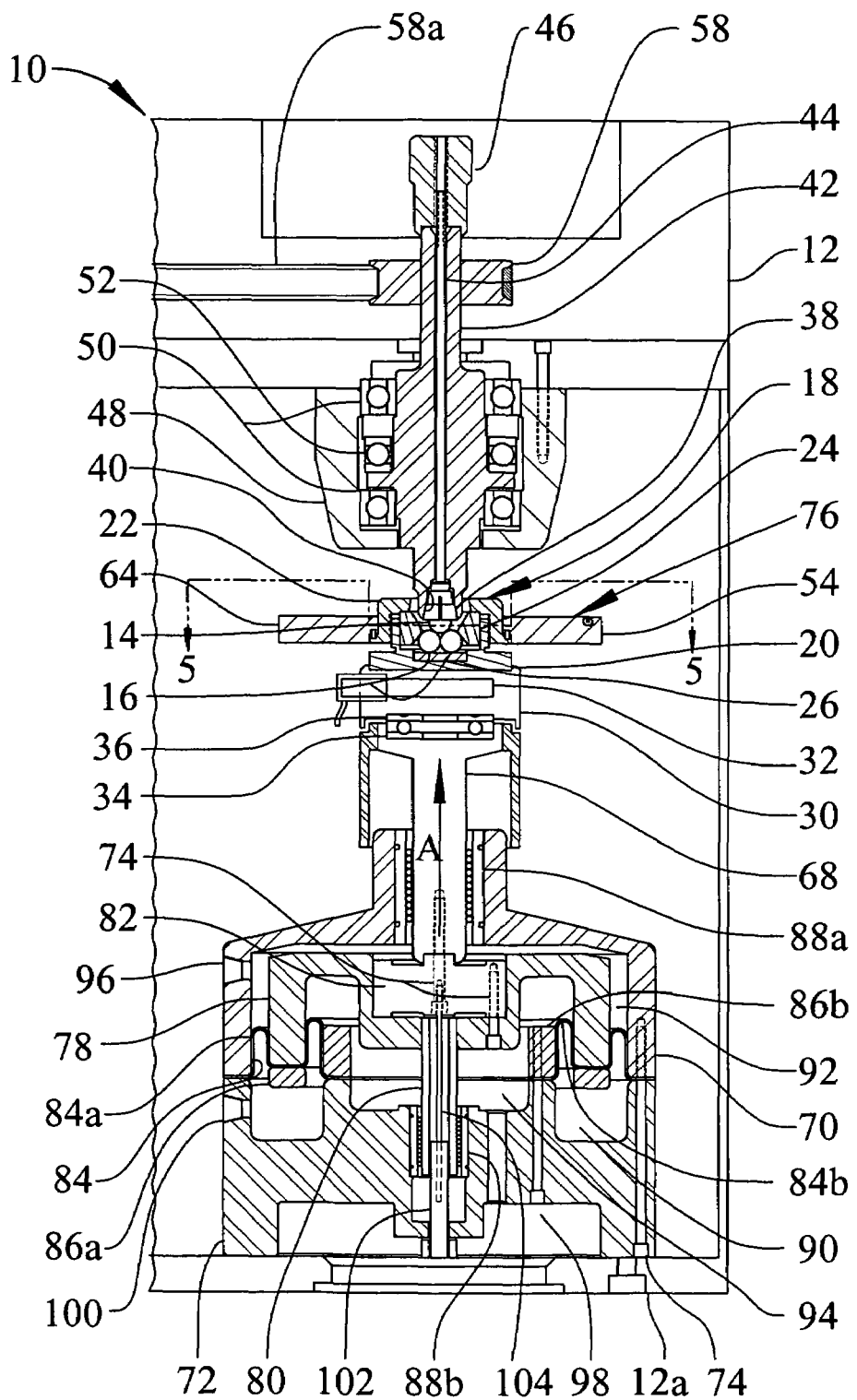
FIG. 3 is cross-sectional view taken substantially through the center of the test machine of FIG. 1, and showing the machine and test balls as during a test.

For purposes of illustration, the present invention is shown in the drawings as a four-ball test machine 10 (FIG. 1) adapted for testing wear, wear-preventative and friction characteristics of lubricants and materials by rotating a test ball 14 (FIG. 3) against three stationary balls 16 under predetermined time and compressive load test conditions.

The test machine is also suitable for testing (i) wear and friction properties of non-lubricated balls, and (ii) other specimens shapes such as washers and discs when provided with suitable adapters.

In this instance, the three non-rotated, generally stationary test balls 16 are firmly held in a ball-pot assembly 18 that includes a ball pot 20 capable of holding lubricant to immerse the balls during the test. A lock nut 22 threaded onto the ball pot acts against a tapered ring 24 to secure the balls 16 in the assembly between the ring and a hardened thrust plate 26.

The ball pot assembly 18 rests on a mounting disc 30 which is mounted to an axial thrust bearing 34 for independently angular mobility of the mounting disc and ball pot assembly between the thrust bearing and the rotated ball 14. The upper race 36 of the thrust bearing is inverted to enable lateral shifting of the mounting disc and ball pot assembly to assist in maintaining the stationary balls laterally centered on the rotated ball during a test.

Preferably, the mounting disc 30 is provided in the form of an aluminum block and one or more electrical heating elements such as the cartridge heater 32 shown extending into the block and electrically connected to the machine controls 110 to define a heater unit. The heater is used to preheat the lubricant prior to testing, and/or maintain the lubricant at a desired temperature during a test.

Figure 4:
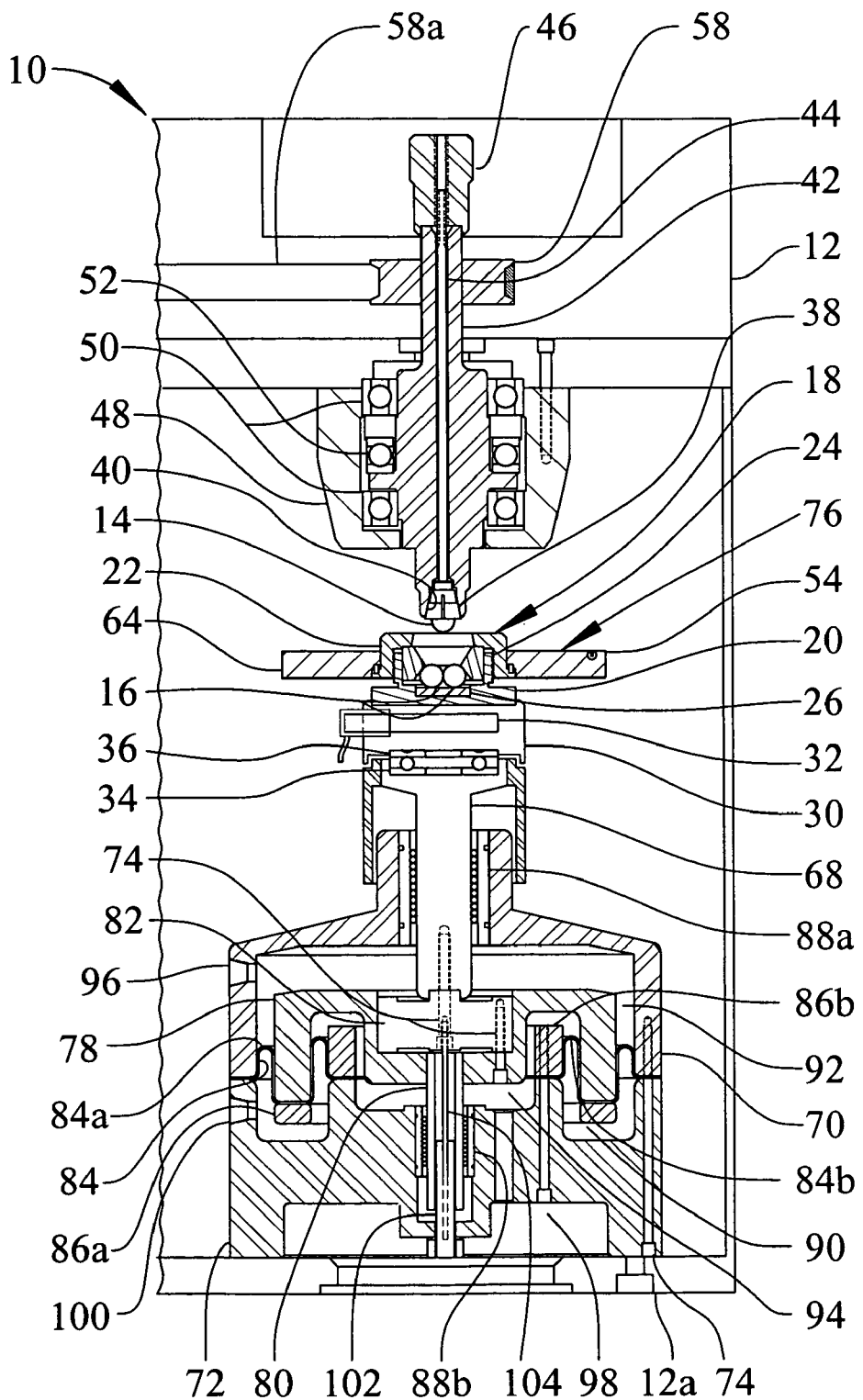
FIG. 4 is a view similar to FIG. 3 but showing the load mechanism and associated components in a retracted position.

With the load mechanism in a retracted position (as shown in FIG. 4), the ball pot assembly 18 is removable from the machine 10 for examination and replacement of the test balls, or for providing suitable adapters for the collet and to rest on the mounting disc for testing alternate shape specimens.

The rotated test ball 14 is operatively coupled to an electric motor (not shown) for rotation such as indicated by arrow "C" in FIG. 1 during the test. In the embodiment shown, the rotated test ball 14 is located in a ball chuck/collet 38 formed with radially compliant jaws that retract inwardly as the collet is drawn into a tapered collet seat 40 defined integrally at one end of a rotary drive shaft 42.

A draw bar 44 extending from the collet 38 through the center of the drive shaft 42 is threaded into a threaded cap/knurled nut 46 such that manual rotation of the nut against the end of the drive shaft pulls the draw bar through the shaft and the collet snugly into the collet seat, causing the collet jaws to collapse and grip the test ball 14.

The drive shaft 42 is rotatably supported in a spindle housing 48 connected to the machine frame 12, with radial bearings 50 and axial thrust bearings 52 therein for supporting the drive shaft.

The electric motor is coupled to the drive shaft such as through belt 58a and pulley 58 to power rotate the shaft and the test ball in the collet.

The machine frame 12 provides the necessary support for the various components of the test machine, and is structurally adapted to carry and react the compressive test loads during a test. To that end, the machine includes upper, lower, front and back members, including a base plate 12a, upper plate 12e, a back plate 12d, and front tension posts 12c.

Figure 7:
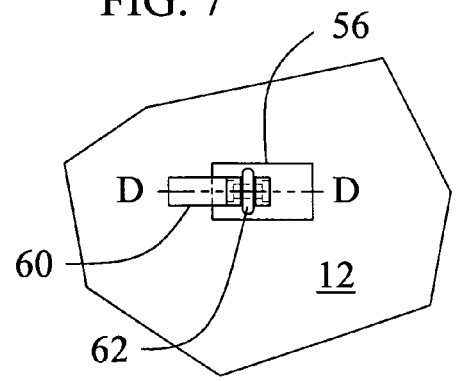
FIG. 7 is a fragmentary view taken along the line 7—7 of FIG. 5.

A torque sensor assembly 76 is connected to the ball pot assembly 18 for measurement of the torque generated by the friction between the rotating ball 14 and the stationary balls 16 during the test. In the embodiment shown, the torque sensor assembly includes a torque lever arm 54 that is snugly connected to (such as with pins shown) and extends radially outwardly from the lock nut 22 for angular rotation therewith, and that is operably coupled to force transducer 56 (FIG. 7).

Figure 5:
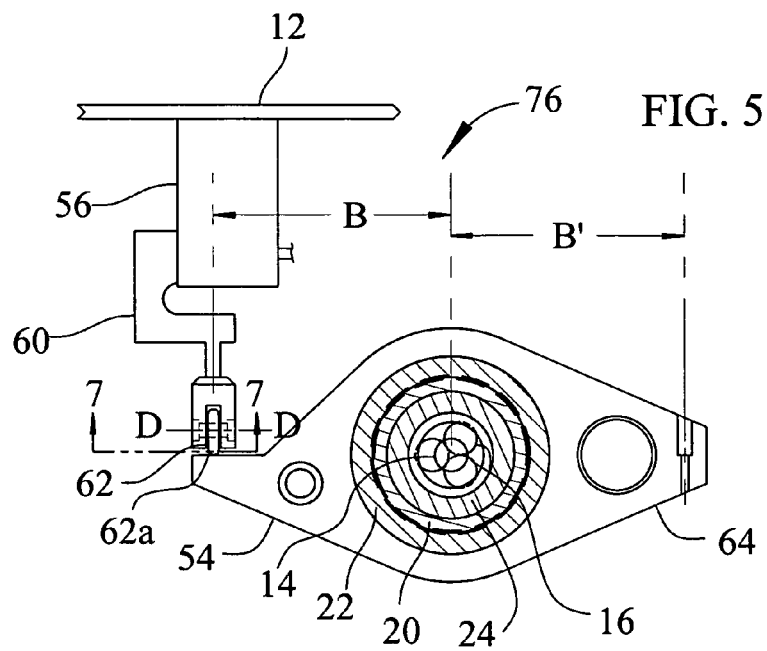
FIG. 5 is a fragmentary view taken substantially along the line 5—5 of FIG. 3.

The force transducer 56 is connected to the frame 12, with a connecting member 60 of the transducer (see FIG. 5) that is adapted to transmit the angular movement of the torque lever arm in the form of linear movement for detection by the transducer.

A rolling member 62 such as a wheel or ball bearing, preferably provided with an outer radius profile 62a when viewed from above, is pivotally mounted on a horizontally extending axis D—D in the connecting arm to provide for a rolling contact interface between the torque lever arm and the connecting arm.

The rolling interface accommodates axial movement of the torque lever arm (i.e., up and down) as the balls 14 and 16 wear and the ball pot assembly 18 shifts axially during a test, without affecting translation of the angular movement of the arm 54 into linear movement of the connecting arm 60. In other words, the radius 62a assists to maintain the torque lever distance "B" accurately, independently of movement during a test.

Figure 6:
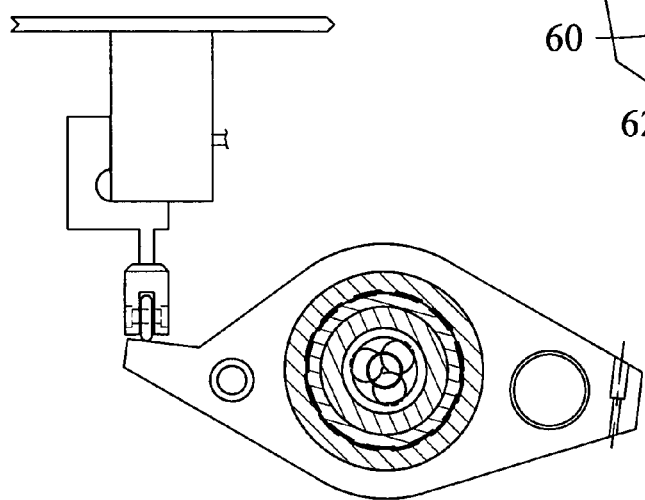
FIG. 6 is a view similar to FIG. 5 but showing a torque sensor mechanism in a rotated position.

As shown in FIG. 6 (wherein a normal rotation of only a few thousandths of an inch is shown exaggerated), the outer radius profile 62a assists in maintaining good rolling contact at the torque arm distance "B" as the torque lever arm 54 pivots due to friction during a test.

With the force transducer 56 acting over a know length "B" (FIG. 5), i.e., the distance between the center of the ball pot assembly 18 and the contact point with the rolling member 62, the output signal from the force transducer is calibrated and/or electronically processed to provide an output signal indicative of the torque generated by friction between the balls during a test.

Figure 9:
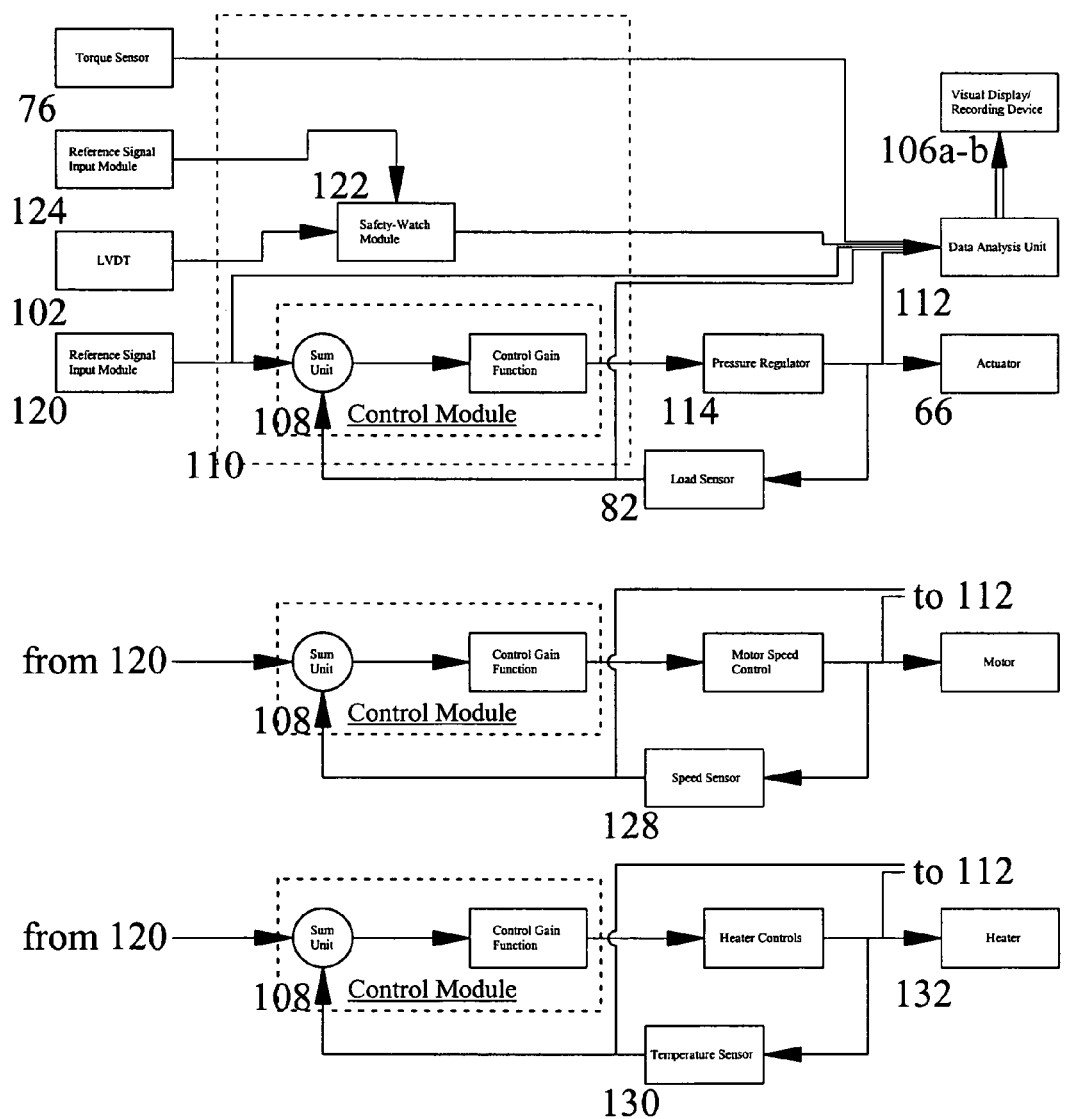
FIG. 9 is a diagrammatic view generally showing signal relationships between certain components, including a feedback control module and safety-watch module, of the test machine.

This output signal is then provided to one or more of (i) a visual read-out 106a or recording device 106b shown as a print-out device, (ii) an electronic control module 108 (FIG. 9) in a control unit 110, and (iii) a data analysis unit 112.

An optional second arm 64 extending from the torque lever arm 54 aids in calibrating the force transducer 56 by enabling application of a known weight over the same lever arm length B', and for ease of checking the calibration of the transducer in a laboratory.

A pneumatic diaphragm actuator 66 applies the axial load condition to the balls 14 and 16 during a test. The actuator is grounded (i.e., firmly connected in load-transmitting relation) to the machine frame 12 and is operatively connected to the ball pot assembly 18 through a linearly acting load rod 68.

The load rod is supported in a linear bearing 88*a* for low-friction linear movement, but is rotationally isolated from the ball pot assembly by the axial thrust bearing 34 such that frictional torque generated between the balls during a test is not transmitted into the actuator.

In the embodiment shown, the actuator 66 includes a housing 70, a base 72 secured thereto such as with angularly spaced threaded fasteners generally indicated with reference numeral 74, and a piston assembly responsive to pneumatic pressure supplied to pressure chamber 90.

The piston assembly includes a piston 78, a guide tube 80 operably coupled to the load rod 68 for linear axial movement together, and an elastimeric rolling diaphragm 84 connected to the piston. The diaphragm is provided with radial outer and inner rolling portions, 84*a* and 84*b*, respectively, to provide for the annular pressure chamber 90 so as to permit extension of a wear sensor 102 (discussed further below) through the center thereof.

In this instance, an outer diaphragm retaining ring 86*a* secures the diaphragm between the rolling portions 84*a*, 84*b* to the piston 78, the outer diameter portion of the diaphragm is secured between the housing 70 and the base 72, and the inner diameter portion is secured to the base with a second retaining ring 86*b*, such as with angularly spaced threaded fasteners 74, and such that the annular pressure chamber 90 is defined therebetween.

An air inlet port 100 in the base provides communication to the annular chamber 90. The outer and inner actuator chamber 92 and 94 are vented to atmosphere at 96 and 98, respectively.

As air pressure is introduced into the annular chamber 90, the differential pressure acting over the effective area on the diaphragm 84 actuates the piston 78 toward the ball-pot assembly 18 as indicated by arrow A in FIG. 1. The force of the pressure acting on the diaphragm results in a compressive test load between the test balls as they approach and engage one another.

The compressive test load is reacted against by the drive shaft 42, as indicated by arrow A' in FIG. 1, which, is grounded to the machine frame 12 through the bearings 50, 52 and the spindle housing 48 as discussed above.

The actuator is preferably sized to provide an accurate load range between approximately 13 kg and 1000 kg, with the available air supply pressure, such that the test machine 10 is capable of conducting both conventional wear testing and extreme pressure testing.

When pressure is relieved from the actuator 66, gravity (or with the assistance of an optional spring between the piston 78 and the upper portion of the housing 70 in chamber 92) returns the piston assembly to its retracted (i.e., down) position as shown in FIG. 4.

As will be evident to those skilled in the art, the load-generating actuator may alternately be, for example, a pneumatic actuator of alternate construction, or a hydraulic actuator with appropriate pressure supply and hydraulic circuit components associated therewith.

A load sensor 82, such as of a commercially available type, is connected directly in the load path of the test machine 10, preferably in-line with the load applied to the test specimens along axis A—A'. In the embodiment shown, the sensor is connected between piston 78 and the load rod 68.

The load sensor 82 directly measures and provides an electric output signal indicative of the compressive force developed in the actuator 66 and transmitted to the test balls 14 and 16.

This output signal is then electronically processed and/or provided to one or more of (i) a visual read-out 106*a* or recording device 106*b* shown as a print-out device, (ii) an electronic control module 108 in a control unit 110, and (iii) a data analysis unit 112.

Advantageously, the output signal from the load sensor is a direct indication of the actual real-time compressive load conditions between the test balls.

A linear position/movement sensor is connected to directly track the wear between the balls 14 and 16 during a test, and is preferably located aligned with the test-load axis A—A'. In the embodiment shown, the wear sensor is provided in the form of an LVDT 102 located in the actuator base 72, with its plunger 104 connected to the center of the load sensor 82 for linear movement therewith.

Thus, the linear sensor 102 is connected to and directly measures and provides an electric output signal indicative of the linear movement of the load path components, and thus a direct indication of linear/axial ball wear on a real-time basis during the test.

The output signal from the LVDT is electronically processed and/or provided to one or more of (i) a visual read-out 106*a* or recording device 106*b* shown as a print-out device, (ii) an electronic control module 108 in a control unit 110, and (iii) a data analysis unit 112.

A pressure regulating valve 114 connected to inlet port 100 of the actuator 66 controls the pressure supplied to the pressure chamber 90. The pressure regulating valve is either manually operable such as with handle 116, and/or electrically controllable and connected to the control unit 110. An air pressure source such as "shop air" is connected to the regulator such as indicated at 118 for supplying pressurized air thereto.

In the case of a manually operable regulating valve, the pressure is adjusted to obtain the desired load conditions between the balls prior to running a test. Visual information from a device such as 106*a* enables the load conditions to be precisely and repeatably established between different test setups, and if desired, enables manual adjustment of the load conditions during a test.

The electronic control unit 110 provides automated control of the load conditions both before and during a test. The control unit receives an input reference signal from an input reference signal generating module 120. The input reference signal caries information as to desired load conditions on the test balls, as well as setpoint information on additional test parameters such as desired test speed and temperature. The control unit then controls the pressure in the actuator based on this reference signal to develop those desired load conditions.

Figure 8:
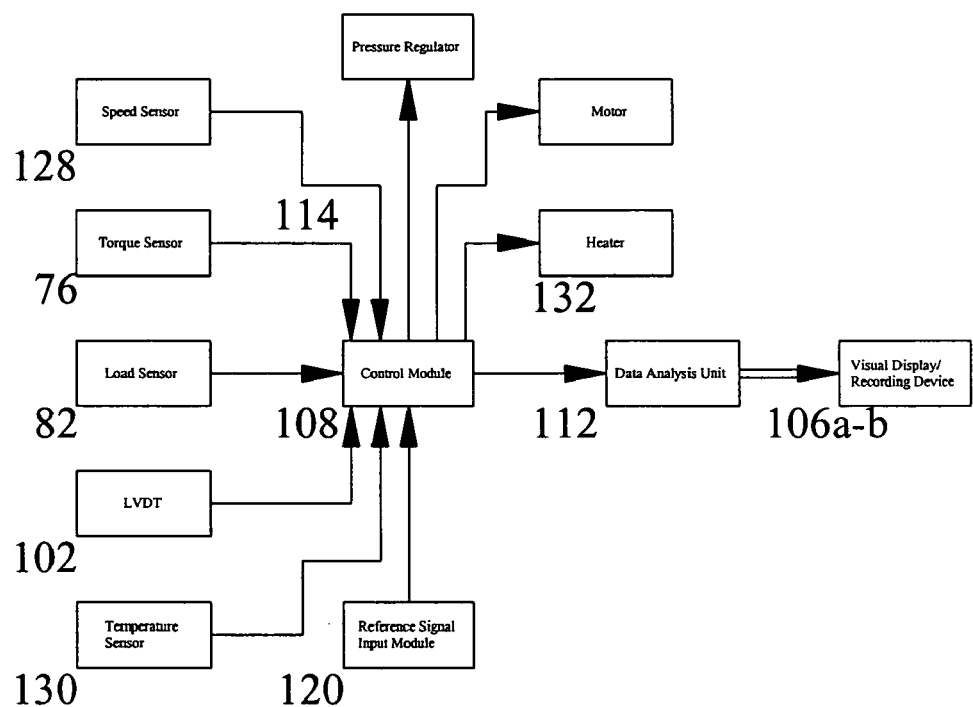
FIG. 8 is a diagrammatic view generally showing signal relationships between certain components of the test machine.

In preferred embodiments, the control unit 110 includes a closed-loop feedback control module 108 that receives a signal indicative of the actual load conditions from the load sensor 82, compares the actual load conditions to the reference signal, and adjusts the output control signal to the pressure regulator 114 to reduce the error therebetween toward zero. This arrangement is generally, diagrammatically illustrated in FIGS. 8 and 9.

The input reference signal to the control unit 110 is provided with a module 120 adapted for either manual entry of the desired set-point information (e.g. with a potentiometer, dip switches, etc.) or for automated entry such as downloaded with a data port or input with a keyboard module.

Advantageously, the input module 120 can be programmed to provide both variable load profiles and constant load profiles during a test. For example, for conducting a weld-point test, the input signal module can be programmed to provide a reference signal that increases at a controlled rate during the test until the balls seize together. Alternately, the input signal module can be programmed to provide other load profiles during a test. Similarly, the setpoint profiles of the other test parameters can be provided either as constant or variable profiles.

In preferred embodiments, the control unit 110 also includes a safety-watch module 122 adapted to monitor various test conditions, and to shut-down the test if those conditions are present.

For example, in preferred embodiments, the LVDT output signal is provided to the safety-watch module which compares it to a reference position signal from a reference signal input module 124 that stops the testing as the linear wear approaches the point where the rotating ball chuck 38 could contact the stationary balls 16, thereby precluding the possibility of damage to the machine therefrom.

The electronic control unit 110 also receives input signals indicative of the speed of the rotated test ball 14 and the temperature of the heater and/or lubricant under test, from appropriately located speed sensor 128 and temperature sensors 130, for automated control of the test temperature developed by the heaters 32 and speed of the electric motor as compared with the setpoint signals therefor.

In preferred embodiments, the test machine 10 also includes an electronic signal processing/data analysis unit 112 for receiving and processing data signals from the test, and to provide desired data therefrom. For example, in the embodiment shown, the data analysis unit is connected, either directly or through the control unit 110, to receive signals such as from the LVDT 102, the torque sensing unit 76, the pressure in the actuating chamber 90, the rotational speed sensor 128, the temperature sensor 13, and the load sensor 82, and is adapted for further processing, manipulation and/or comparison of such data to obtain and provide additional test performance indicators such as: linear wear of test balls vs. time, linear wear of test balls vs. cycles, linear wear of test balls vs. speed of rotation, linear wear of test balls vs. temperature of lubricant, linear wear of test balls vs. load characteristics for static load changes, linear wear of test balls vs. load characteristics for dynamic load changes, torque generated between the stationary and rotating balls, frictional forces generated and coefficient of friction developed between the test balls, and additional test parameters and indicators of wear, wear-preventative, friction and lubrication properties.

When provided with, for example, static load compressive data and thermal expansion data for material of the balls under test, the data analysis unit is adapted to bias out expansion due to temperature changes in the test balls as controlled by the heater assembly, and compression of the test balls, chuck, spindle and rotary drive shaft interface to arrive at actual dimensional linear wear data.

The results from the data analysis unit are then provided to the operator in a form suitable for subsequent uses, such as in an electronic data file or an electrical signal suitable for graphical and/or printed representation therefrom.

From the foregoing, it will be apparent that the present invention brings to the art a unique arrangement for a test machine of the type suitable for testing wear, wear-preventative and friction characteristics between a rotating specimen axially loaded against one or more stationary test specimens. The in-line, directly acting, pneumatic diaphragm actuator loading arrangement of the invention allows for a greater load-test capacity range between the rotating ball and stationary balls as compared with prior conventional four-ball testing arrangements. The preferred pneumatic actuator with rolling diaphragms provides for an especially low friction, low hysteresis load mechanism, thus enabling enhanced resolution of load control during testing, and reduced error producing inaccuracies, resulting in controlled, repeatable loading conditions for different tests as compared with prior conventional four-ball testing machines. The direct sensing load sensor aligned in the load path of the test specimens provides accurate test load conditions and enhances load control when used for visual feedback to the operator and/or in an automated feedback control system. And the direct sensing linear wear sensor provides accurate linear wear information, the ability to protect the test machine from damage resulting from excessive wear, and the ability to evaluate additional wear, wear-preventative, friction and lubrication characteristics with the test machine.

I claim:

1. A test machine adapted to test wear, wear-preventative and friction characteristics of a power-rotated first test specimen engaging a non-rotated second test specimen, the test machine comprising:
   a chuck connected for power rotation of the first test specimen about an axis;
   a holder adapted to hold the second test specimen in a position engageable with the first test specimen;
   a force actuator connected for positioning the holder along said axis, the actuator being operable to establish a compressive test load between the test specimens, and
   a linear wear sensor connected aligned with said axis to measure and provide an output signal indicative of the real-time linear movement of the test specimens during a test.

2. The test machine as defined in claim 1 in which the force actuator comprises a pneumatic diaphragm actuator aligned along said axis.

3. The test machine as defined in claim 1 in which the wear sensor is connected to said actuator for axial movement therewith and for direct detection of axial movement thereof.

4. The test machine as defined in claim 3 in which the wear sensor is connected in-line along said axis.

5. The test machine of claim 1 further comprising a torque sensor operably connected to the holder for sensing the frictional torque generated between the test specimens during a test.

6. The test machine as defined in claim 1 further comprising at least one of a visual display module and an automated control module, the wear sensor being connected to said at least one module and providing an output signal thereto indicative of the real-time linear movement of the test specimens during the test.

7. The test machine as defined in claim 6 in which the wear sensor is connected to the control module, and further comprising an input reference module connected to supply a reference wear signal to the control module, the control module being operably connected to the actuator and adapted to adjust the compressive test load established therein according to the relationship between the reference wear signal and the output signal from the wear sensor.

8. The test machine as defined in claim 1 further comprising a data analysis module connected to the wear sensor and adapted to numerically manipulate an output signal therefrom for determining one of a wear, wear-preventative and friction characteristic relationship therewith.

9. A test machine to test the wear, wear-preventative and friction characteristics of a power-rotated first test specimen engaging a non-rotated second test specimen, the test machine comprising:
- a chuck connected for power rotation of the first test specimen about an axis;
- a holder linearly movable along said axis to hold the second test specimen in a position engageable with the first test specimen;
- a pneumatic diaphragm actuator connected in-line with said axis to position the holder along said axis and establish a compressive test load between the test specimens during a test;
- a load sensor connected in-line with said axis in the load path between the actuator and the holder to directly measure and provide an output signal indicative of the real-time compressive forces applied to the test specimens during a test; and
- a linear wear sensor coupled for linear movement in-line with said axis and with the diaphragm actuator and for direct measurement of linear movement thereof.

10. The test machine as defined in claim 9 further comprising an automated control module connected to the load sensor and an input reference module connected to supply a reference load signal to the control module, the load sensor providing an output signal to the control module indicative of the real-time compressive forces applied to the test specimens during the test, and the control module being operably connected to the diaphragm actuator to adjust the compressive test load established therein according the reference load signal and the real-time output signal from the load sensor.

11. The test machine as defined in claim 9 further comprising a torque sensor operably connected to the holder and providing an output signal indicative of the frictional torque generated between the test specimens during a test.

12. The test machine as defined in claim 9 further comprising a data analysis module connected to the load sensor and the linear wear sensor to numerically manipulate the output signals therefrom for determining one of a wear, wear-preventative and friction characteristic relationship with the compressive test load.

13. The test machine as defined in claim 9 further comprising a temperature control heating element connected to the holder.

\* \* \* \* \*